United States Patent [19]

Kinney

[11] 4,300,551
[45] Nov. 17, 1981

[54] METHOD FOR TREATING SCHIZOPHRENIA

[76] Inventor: Michael J. Kinney, Suite 909 - Mt. Huntington, Huntington, W. Va. 25701

[21] Appl. No.: 72,718

[22] Filed: Sep. 4, 1979

Related U.S. Application Data

[63] Continuation-in-part of Ser. No. 902,729, May 2, 1978, abandoned.

[51] Int. Cl.³ ............................................ A61M 5/00
[52] U.S. Cl. .................................. 128/214 R; 128/637
[58] Field of Search .................. 128/1 R, 214 R, 637; 210/24, 40, DIG. 23

[56] References Cited

U.S. PATENT DOCUMENTS 3,888,250  6/1975  Hill .................................. 128/214 R

OTHER PUBLICATIONS

"Hemodialysis in Chronic Schizophrenic Patients", Wagemaker et al., *Southern Medical Journal*, vol. 71, #12, Dec. 1978.
"Haemodialysis with Charcoal Haemoperfusion", *Proc. Eur. Dial. Transplant Assoc.*, Winchester et al., 12: 526–533, 1976.
"Can Dialysis Help The Chronic Schizophrenic?" *Am. J. Psychiatry* Nov. 1977.
"Hemodialysis for Schizophrenia", *Dialysis & Transplantation*, Jan. 1979, Levy.
"The Effect of Hemodialysis on Schizophrenia", *Amer. J. Psychiatry*, Port et al., Jun. 1978.
"The Comparitive Effects of Placebo, Ultran, and Meprobamate on Psychologic Test Performances", Antibiotic Med. & Clinical Therapy", vol. 4, 1957, Reitman.

*Primary Examiner*—Robert W. Michell
*Assistant Examiner*—Thomas Wallen
*Attorney, Agent, or Firm*—Kinney & Niblack

[57] ABSTRACT

A method for treating schizophrenia in human patients by hemoperfusion using hemoperfusion of the patient's blood through a charcoal cartridge in a manner for selective removal of molecules is disclosed. The method may use known hemoperfusion cartridges for a heretofore completely unappreciated application and has the advantages of lesser side effects and easier implementation than other known methods of treatment.

9 Claims, 2 Drawing Figures

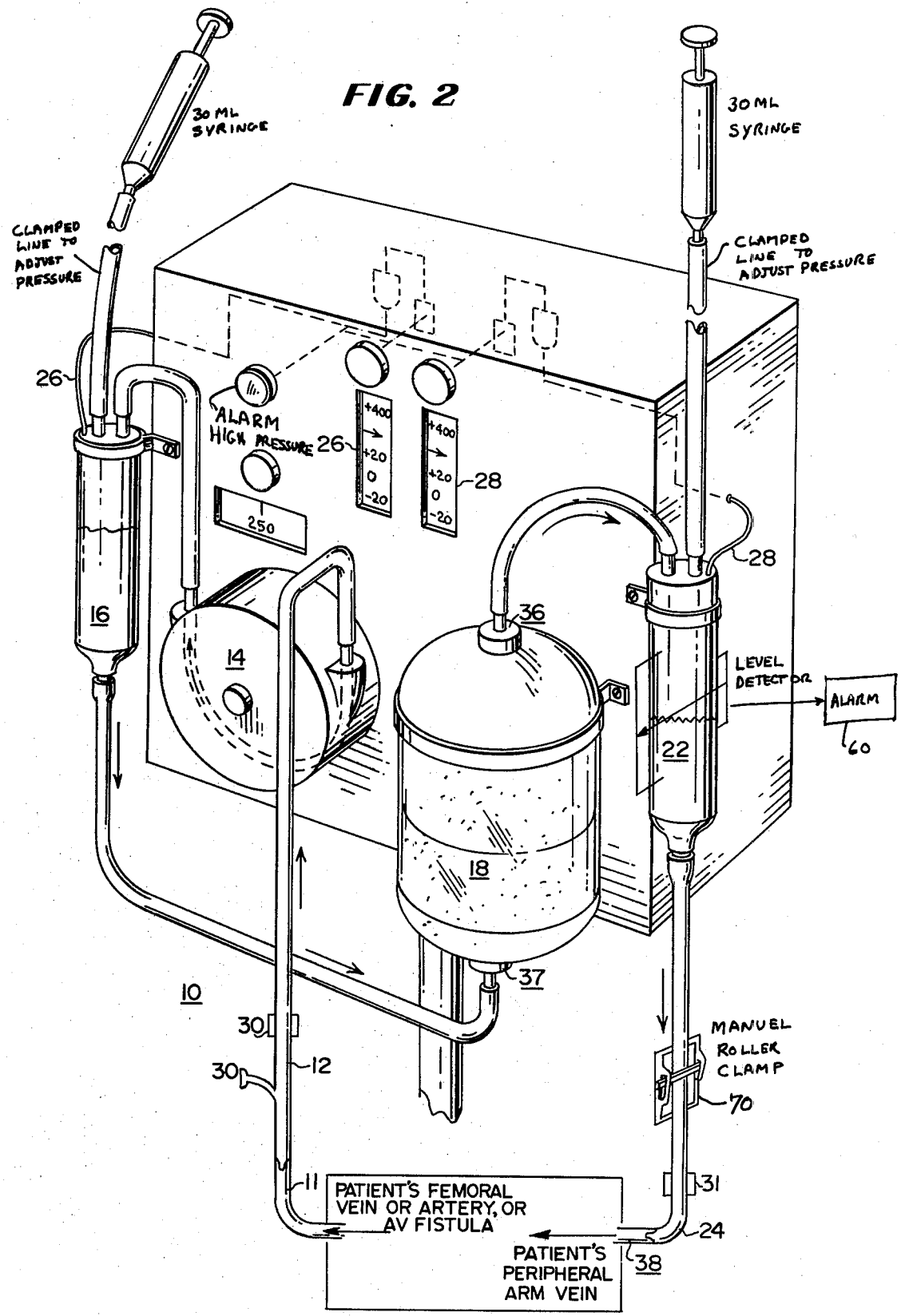

METHOD FOR TREATING SCHIZOPHRENIA

CROSS-REFERENCE TO RELATED APPLICATION

This is a continuation in part of application Ser. No. 902,729 entitled "Method for Treating Schizophrenia" and filed on May 2, 1978, now abandoned.

The present invention relates to a new method of treating schizophrenia and is particularly directed to a novel process for the patient's blood chemistry.

BACKGROUND OF THE INVENTION

Schizophrenia is generally considered and is defined by Merriam-Webster's Third International Dictionary as a psychotic disorder of unknown complex etiology that occurs as simple, paranoid, catatonic, or hebephrenic, and is characterized by disturbances in thinking involving a distortion of the usual logical relations between ideas, a separation between the intellect and the emotions so that the patient's feelings or their manifestations seem inappropriate to his life situation, a reduced tolerance for the stress of interpersonal relations, anxiety, delusions, and hallucinations.

In the United States at the present time, it is estimated that schizophrenic patients occupy more hospital beds than any other illness and that only 20% of schizophrenic patients are hospitalized. One percent of the entire population of the United States has been labeled schizophrenic.

It has been discovered that some schizophrenic patients respond favorably to treatment by hemodialysis and perhaps two or more toxic metabolities have been identified in the dialysis of schizophrenic patients. There exist, however, several drawbacks in using hemodialysis as a treatment for patients who do not otherwise need dialysis. These include salt and water loss to the patient, hypotension, as well as dialysis handling problems, the problem of cleansing and sterilizing the equipment for re-use, cross infection of non-disposable equipment (hepatitis B), and the problem of possible shock and death from unexpected dialysis coil rupture and blood loss. The present invention avoids these complications while increasing the efficiency of removal of toxic metabolites to more than twice that of dialysis.

SUMMARY OF THE PRESENT INVENTION

In accordance with the present invention, a novel method of treating schizophrenic patients is provided which avoids the above-mentioned problems and drawbacks and attacks the problem of removal of toxins or metabolites directly by using hemoperfusion filtration, preferably with disposable activated adsorbing beds of charcoal in sterile hemoperfusion cartridges with filters and connecting tubing sets. The cartridge of coated or uncoated charcoal should be restrained between filters to prevent the possibility of charcoal embolization into the treated patient's circulation. The charcoal granules need not be fixed to the supports of the cartridge, but may lie loose between the filters.

More particularly, the present invention encompasses the process of treating schizophrenic patients by subjecting them to a series of hemoperfusions of variable duration and frequency depending on the patient's individual responsiveness. The less prolonged and least frequent therapy is the most desirable, but therapy may be as often as three times a week and may be as long as twelve hours. Experience to date with four patients has shown that significant improvement can be expected in most younger patients suffering from chronic schizophrenia if the hemoperfusion be performed only once weekly for 3-4 hours, using only one (1) 300 gram cartridge of coated charcoal, at blood flow rates of 200-250 ml/min, for 8 weeks. Subsequent hemoperfusions may be less frequent; 3-4 hours once a month may suffice.

The invention, together with the advantages thereof, may best be understood by reference to the following description taken in connection with the accompanying drawings, in the figure of which like reference numerals identify like elements.

BRIEF DESCRIPTION OF THE FIGURES

FIG. 2 is a schematic diagram of a second manner of connecting and using a hemoperfusion charcoal cartridge in accordance with the present invention.

DETAILED DESCRIPTION OF FIRST EMBODIMENT

Figure 1:
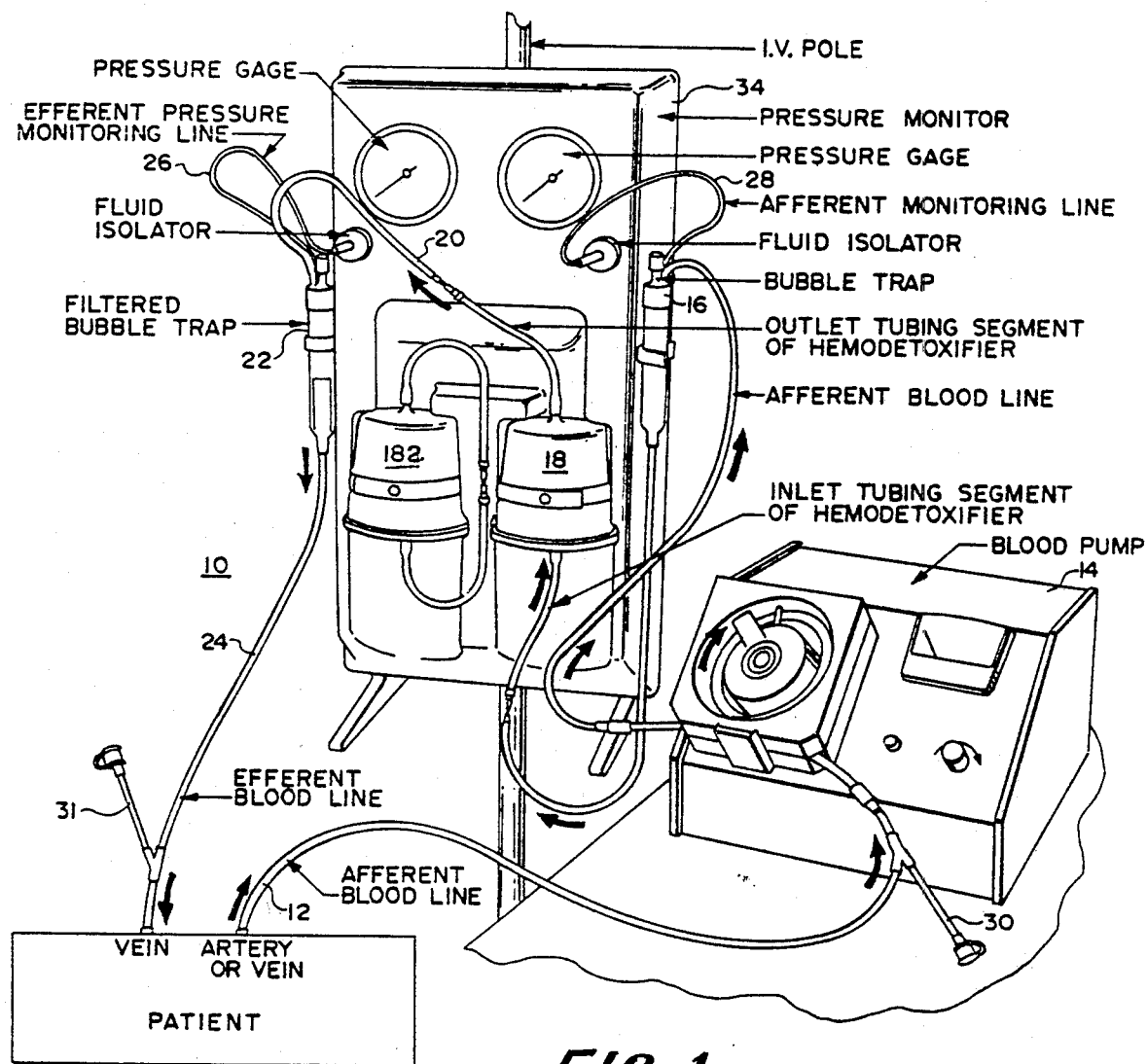
FIG. 1 is a schematic diagram of one manner of connecting and using a hemoperfusion charcoal cartridge in accordance with the present invention.

Referring to FIG. 1, there is depicted a set-adsorption-filter system generally designated 10. The system 10 includes a tube 12 inserted into an artery or vein, which in use passes through a peristaltic pump 14 exterior to the tubing, and feeds through a bubble trap 16 to an activated charcoal adsorption filter cannister 18. From the filter cannister 18, an outlet tubing line 20 leads to a filtered bubble trap 22 and thence through a line 24 to the vein of the patient.

The system 10, including the tubing, filter cannister 18, bubble traps and fittings, such as pressure sensors 26, 28, and sample or input fittings 30, is preferably formed in a closed construction and pre-filled with a charge of sterile saline containing 5000 u heparin U.S.P. per liter. This construction provides a sterile disposable unit 10 that will guard against contamination and possible transfer of diseases, such as hepatitis.

The system 10 is in use preferably as shown, used with an optional pressure monitor unit 34 and positioned as shown above the patient. Sample or input fitting 30, 31 allows for the taking of blood samples; e.g., to monitor concentration of anti-coagulation and injections of drugs and other agents (e.g., glucose).

In technique, the procedures used for hemoperfusion for schizophrenia are those detailed in the literature for hemoperfusion for other uses; for example: Vale et al., Br. Med. J. (5938; 5, 1975), Barbour et al., Kidney Int. 10:S333, 1976.

After insertion of the femoral vein catheter 12 and peripheral vein catheter 24 and starting of the blood pump, 5000 additional units of heparin are given through tap site 30. Clotting times of blood drawn from tap site 30 will dictate the rate of addition of further heparin through site 30 by use of a sterile N. saline solution containing 5000 u heparin/liter attached to tap site 30 and infusing at about 1.0 ml/min. The exact infusion rate depends on Lee-White clotting times: maintained at 30-40 min. The pressure differential across the charcoal cartridge will be <90 mm Hg. Higher pressures will dictate a change of cartridge or discontinuation of therapy. Cartridges will be used for only 3 hours and 2 cartridges may be used consecutively in a projected weekly customary treatment (6 hours). The second cartridge and its tubing will be flushed with 3000 ml. of Saline (5000 u heparin/liter)—just as the first—prior to its replacement of the first cartridge in the closed extracorporeal circuit. For the 6 hours of hemoperfusion the patient may receive through blood tap 2 (31) a slow infusion of 5% dextrose in water intravenous feeding (500 ml). During the final 2 hours of this infusion, 10 ml. of a 10% calcium gluconate solution may be added to the remaining 200 ml. of 5% D/W for slow infusion.

Following 6 hours of therapy, the patient's blood in the extracorporeal circuit is preferred to be returned to him/her by rinsing a liter of N. saline by gravity drip through the dircuit from tap site 30. Catheters and tubing and cartridge will then be removed from the patient and usually pyrolyzed. However, some cartridges may be leached for study of their adsorbed materials. The patient's femoral site of venous or arterial puncture will be firmly compressed for 10 minutes.

The patients may remain in bed under close observation after hemoperfusion is completed. They will eat and each preferably will drink at least 2 glasses of milk. Afterward, the patients will then be allowed to ambulate and, if indicated, some may remain hospitalized overnight (18 hours) for observation.

Although a cartridge-set system is preferably pre-packaged, the method can be used using existing equipment. A suitable cartridge 18 or 18a is the presently available B-D Hemodetoxifier such as is commercially available and used for treatment of drug poisoning. Such a unit and its use is disclosed in the publication *Charcoal Hemodetoxification, A New Clinical Tool for the Treatment of Drug Poisoning* by B. H. Barbour, M.D., published by Becton, Dickinson and Company in 1975, and also Operation Manual No. 09100083-01C, also published by the Becton, Dickinson Company in 1975. Another cartridge that may be employed is the Hemocol ™ Activated-Charcoal Hemoperfusion Column made by the Warner/Chilcott division of Warner-Lambert Company.

Referring to FIG. 2, there is depicted a charcoal cartridge set-adsorption-filter system, generally designated 10. The system 10 includes a sterile catheter 11 inserted into an artery or vein, preferably the femoral vein, which in turn is connected to tubing 12, which in use passes through a pump 14 exterior to the tubing and feeds through a bubble trap 16 to an activated charcoal adsorption-filter cartridge 18. From the filter cartridge 18, an outlet tubing line 20 leads to a filtered bubble trap 22, with a level detector-monitor to an automatic external line safety clamp, thence through a line 24 to the vein of the patient, at which it may be connected to another catheter.

The system 10, including the tubing, filter cartridge 18, bubble traps and fittings, such as pressure sensors 26, 28 and sample or input fittings 30 (for sterile needle external access to the blood flow), is preferably formed in a closed construction and pre-filled with a charge of sterile saline containing 5000 u heparin U.S.P. per liter. Before filling with saline, it is rinsed with Dextrose in Water to minimize uptake of the patient's blood sugar (pre-saturation of the charcoal for sugar). This construction provides a sterile disposable unit 10 that will guard against contamination and possible transfer of diseases such as hepatitis.

The system 10 is in use preferably as shown, used with optimal pressure monitors 26 and 28, and positioned as shown above the patient. Sample or input fitting 30, 31 allows for the taking of blood samples; e.g., to monitor concentration of anti-coagulation and injection of drugs and other agents (e.g., heparin). However, the unit 10 does lend itself to being utilized in 3 subsections: (1) the extracorporeal circuit of line fittings, bubble trap, and monitor prior to (in blood flow direction) the charcoal cartridge, (2) the same subsequent (in terms of blood flow direction) to the cartridge, and (3) the cartridge (18). If utilized in this modular manner, it is possible to exchange sterile subsections which may prove defective, experience clotting, etc., by separating the subsections at fittings 36 or 37: screw type fittings. Careful attention to aseptic standard medical techniques is necessary for such exchanges, as it is for the dual catheterizations of the patient.

In technique, the procedures used for hemoperfusion for schizophrenia are those detailed in the literature for hemoperfusion for other uses; for example: Vale et al. Br. Med. J. (5938; 5, 1975), Barbour et al., Kidney Int. 10:S333, 1976.

After insertion of the femoral vein catheter and peripheral vein catheter 38 and starting of the blood pump, 5000 additional units of heparin are given through tap site 30. Clotting times of blood drawn from tap site 30 will dictate the rate of addition of further heparin through site 30 by use of a sterile N. saline solution containing 5000 u heparin/liter attached to tap site 30 and infusing at about 1.0 ml/min. The exact infusion rate depends on Lee-White clotting times: maintained at 30–40 min. The pressure differential across the charcoal cartridge will be 90 mm Hg. Higher pressures will dictate a change of cartridge or discontinuation of therapy. Cartridges will be used for only 3–4 hours. Two cartridges may be used consecutively in the projected initial series of 8 weekly treatments (6 hours) by separating at 36 and 37. However, to date, one cartridge for 3–4 hours has proved sufficient. The second cartridge and its tubing will be flushed with 3000 ml. of saline (5000 u heparin/liter)—just as the first—prior to its replacement of the first cartridge in the closed extracorporeal circuit. For the period of hemoperfusion therapy or shortly thereafter, the patient may receive through blood tap 2 (31) a slow infusion of 500 ml. of 5% dextrose in water (5 Gms/100 ml.) intravenous feeding. During the final hour of this infusion, 10 ml. of a 10% calcium gluconate solution (10 Gm/100 ml.) may be added to the dextrose in water for slow infusion. 20–40 minutes before discontinuing hemoperfusion, the heparin infusion is discontinued.

Following hemoperfusion, the patient's blood in the extracorporeal circuit is preferred to be returned to him/her by rinsing a liter of N. saline by gravity drip through the circuit from the catheter connecting site at 11 through tube 24 and catheter or needle 38 into the patient. Catheters, tubing, and cartridge will then be removed from the patient and usually pyrolyzed. However, some cartridges may be leached for study of their adsorbed materials. They will not be re-used. The patient's femoral site of venous or arterial puncture will be firmly compressed for 10 minutes or longer.

The patients remain in bed under close observation after hemoperfusion is completed for one hour. They eat and take fluids. After one hour, the patients are allowed to ambulate, but, if indicated, some may remain hospitalized overnight (18 hours) for observation.

Although a cartridge-set system is preferably pre-packaged, the method can be used using existing equipment. A suitable cartridge 18 is the presently available B-D Hemodetoxifier such as is commercially available and used for treatment of drug poisoning. Such a unit and its use is disclosed in the publication, *Charcoal Hemodetoxification, A New Clinical Tool for the Treatment of Drug Poisoning*, by B. H. Barbour, M.D., published by Becton, Dickinson and Company in 1975, and also Operation Manual No. 09100083-01C, also published by the Becton, Dickinson Company in 1975. Another cartridge that may be employed is the Hemocol TM Activated-Charcoal Hemoperfusion Column made by Smith and Nephew in England and distributed by The Warner/Chilcott division of Warner-Lambert-/Parke-Davis Company in the U.S. A third charcoal cartridge is available from Gambro, Inc. and is labeled the Adsorba 300C. Until this inventor's suggestion and use of the cartridge for this illness, schizophrenia, its only medical uses have been in rare cases of renal or hepatic failure and occasional cases of drug overdoses. No use comparable to the suggested invention has been described or suggested in the medical literature.

As indicated in FIG. 2, it is desirable to adjust the blood pressure across the cannister 18 and to this end variable pressure units such as 30 ml. syringes may be connected via manually clamped tubing to the bubble traps 16 and 22. Flow and pressure into the patient in line 38 may be controlled by an automatic or manual clamp 70. It is also desirable to monitor the blood pressure in the system and to provide for automatic alarms if the pressure detected at line 26 or 28 exceeds a preselected value. Also an optional measuring device to sound an alarm 60 when the level in the input trap 622 falls too low is preferred. Such an alarm may also be keyed to an automatic clamp positioned as is clamp 70 (to prevent the pumping of air or gas into the patient). Such components are well known and need not be described here in detail.

Tubing systems can be patched together from a number of commercial vendors supplying presterilized medical grade tubing. Equipment such as blood pumps, pressure monitors, level detectors, clamps, etc., are also individually available from commercial standard laboratory-medical supply houses.

While two particular embodiments of the intention have been shown and described, it will be obvious to those skilled in the art that changes and modifications may be made without departing from the invention in its broader aspects and, therefore, the aim in the appended claims is to cover all such changes and modifications as fall within the true spirit and scope of the invention.

I claim as my invention:

1. The method of treating schizophrenia in a human patient using a sterile activated carbon medium perfusion filter, comprising the steps of
   (a) forming an extracorporeal blood circulation path from the patient to and through the activated carbon medium filter and back to the patient;
   (b) circulating blood from the patient through that path for a period of time sufficient to capture in the activated carbon medium filter a significant quantity of molecules from the patient's blood, and returning the blood to the patient; and
   (c) repeating the above steps at intervals until the schizophrenic symptoms are lessened, and
   whereby a temporary improvement in the patient's condition may be achieved.

2. The method of claim 1 wherein the activated carbon medium is in a fixed bed array.

3. The method of treating schizophrenia in a human patient using a sterile activated medium hemoperfusion cartridge, comprising the steps of
   (a) forming an extracorporeal blood circulation path from the patient to and through the hemoperfusion cartridge and back to the patient;
   (b) circulating the blood from the patient through that path for a period of time to capture in the cartridge molecules that may represent abnormal metabolites in the patient's blood and returning the cleansed blood to the patient; and
   (c) repeating the above steps at intervals until the schizophrenic symptoms are temporarily improved following such treatment.

4. The method of treating schizophrenia in a human patient using a sterile activated carbon medium perfusion filter, comprising the steps of
   (a) forming an extracorporeal blood circulation path from the patient to and through the activated carbon medium filter and back to the patient;
   (b) circulating blood from the patient through that path for a period of time and returning the filtered blood to the patient; and
   (c) repeating the above steps at intervals until the schizophrenic symptoms are lessened; and
   whereby the patient's schizophrenia is at least temporarily improved.

5. The method of claim 4 wherein the activated carbon medium is in a fixed bed array, and the period of time is at least approximately three hours.

6. The method of claim 4 wherein the period of time is at least approximately three hours.

7. The method of claim 6 wherein the activated carbon medium filter is of the cartridge type.

8. The method of claim 7 wherein the activated carbon cartridge filter has coated charcoal granules in a loose array.

9. The method of claim 7 wherein the activated carbon cartridge filter has coated charcoal granules in a fixed bed array.

* * * * *